(12) United States Patent
Eguchi et al.

(10) Patent No.: US 8,092,383 B2
(45) Date of Patent: Jan. 10, 2012

(54) HEALTH SUPPORT METHOD AND SYSTEM THEREOF

(75) Inventors: Toru Eguchi, Takatsuki (JP); Kiichi Kubota, Hachioji (JP)

(73) Assignee: Sunstar Inc., Takatsuki-shi (JP)

( * ) Notice: Subject to any disclaimer, the term of this patent is extended or adjusted under 35 U.S.C. 154(b) by 0 days.

(21) Appl. No.: 11/547,089

(22) PCT Filed: Mar. 28, 2005

(86) PCT No.: PCT/JP2005/005711
§ 371 (c)(1),
(2), (4) Date: Sep. 18, 2007

(87) PCT Pub. No.: WO2005/096199
PCT Pub. Date: Oct. 13, 2005

(65) Prior Publication Data
US 2008/0040158 A1 Feb. 14, 2008

(30) Foreign Application Priority Data
Mar. 30, 2004 (JP) ................................ 2004-101321

(51) Int. Cl.
*A61B 5/00* (2006.01)
(52) U.S. Cl. .......................................... 600/301; 702/19
(58) Field of Classification Search .................. 600/300, 600/301; 128/903–905, 920
See application file for complete search history.

(56) References Cited

U.S. PATENT DOCUMENTS

| | | | | |
|---|---|---|---|---|
| 6,302,844 B1 * | 10/2001 | Walker et al. | ................. | 600/300 |
| 6,648,820 B1 * | 11/2003 | Sarel | ............................. | 600/300 |
| 2002/0143263 A1 * | 10/2002 | Shusterman | .................. | 600/509 |
| 2003/0101076 A1 * | 5/2003 | Zaleski | ............................. | 705/2 |
| 2003/0135097 A1 * | 7/2003 | Wiederhold et al. | .......... | 600/301 |
| 2003/0229514 A2 * | 12/2003 | Brown | ............................. | 705/2 |
| 2004/0122702 A1 * | 6/2004 | Sabol et al. | ...................... | 705/2 |
| 2004/0225200 A1 * | 11/2004 | Edmundson et al. | ......... | 600/300 |

(Continued)

FOREIGN PATENT DOCUMENTS

JP 2000-99605 4/2000

(Continued)

OTHER PUBLICATIONS

G. Taguchi; "Hinshitsu Kogaku Oyo Koza MT System ni okeru Gijutsu Kaihatsu;" *1st edition; Japanese Standards Association*; 2002; pp. 2-37, cover sheet and end sheet (20 Sheets total.).

(Continued)

*Primary Examiner* — Henry M Johnson, III
*Assistant Examiner* — Kai Rajan
(74) *Attorney, Agent, or Firm* — Kratz, Quintos & Hanson, LLP

(57) ABSTRACT

To provide a method for recognizing/analyzing a plurality of data concerning health management of an individual as his/her personal characteristic pattern data while considering the relationship between the data instead of analyzing each of the data separately; a health support method provided by the method; and a system thereof.

A support computer stores individual health data acquired in advance in individual data storage means and subjects the individual heath data extracted from the individual data storage means to a multivariate analysis, thereby setting a reference space of the individual, which is stored in reference data storage means. For the individual health data received from the user terminal, a Mahalanobis' generalized distance is calculated from the reference space of the individual read out from the reference data storage means and the health condition of the individual is judged according to the distance.

22 Claims, 9 Drawing Sheets

U.S. PATENT DOCUMENTS

2005/0146431 A1 * 7/2005 Hastings et al. ......... 340/539.12

FOREIGN PATENT DOCUMENTS

| JP | 2002-183316 | 6/2002 |
|----|-------------|--------|
| JP | 2003-144406 | 5/2003 |
| JP | 2003-242262 | 8/2003 |
| JP | 2003-319921 | 11/2003 |
| WO | WO 01/95185 A1 | 12/2001 |

OTHER PUBLICATIONS

Notice of Rejection dated Mar. 8, 2011 corresponding to Japanese Patent Application No. 2004-101321.
MT-system and Diagnoses matters.
Utility of Multivariate analysis with English Abstract.

* cited by examiner

HEALTH SUPPORT METHOD AND SYSTEM THEREOF

TECHNICAL FIELD

The present invention relates to a health support method capable of providing a commodity and service suitable for a health condition of each individual and a system thereof.

BACKGROUND ART

There has been proposed a health managing apparatus equipped with an action detecting sensor for detecting the lavatory use state and going-out state of a managed person, life custom recording means for storing history data regarding how often, when, and how long the action detecting sensor operates, judging means for judging the life state of the managed person according to the history data stored in the life custom recording means and the operation of the action detecting sensor, and notice means for outputting periodically the health management data to the outside according to the life state judged by the judging means, thereby preventing an emergency case from occurring, giving notice of even in the case where a trouble which does not reach a level that the system recognizes occurs to the outside before the person himself or herself appeals, and requiring low installation and low operation costs (for example, see Patent Reference 1).

There has been proposed a vital data managing device comprising a vital data receiving part for receiving vital data of each measured person by a vital sensor, a storage part for storing a limit in a normal region of the vital data set in advance by each measured person, a comparing and judging part for comparing the vital data received by the vital data receiving part with the limit value stored in the storage part by each measured person, and judging the abnormality of the vital data when the received vital data exceeds the limit value, a diagnosis data storing part for storing the diagnosis data by each measured person by a primary doctor, and an output file producing part for producing an output file of the abnormality judgement data and the past data for a desired number of shares containing the latest data in the diagnosis data of the person judged to be abnormality stored in the diagnosis data storing part when the comparing and judging part judges the abnormality of the vital data, thereby performing abnormality judgement by simple arithmetic operation and informing a measured person of judgement result on the degree of health with high reliability (for example, see Patent Reference 2).

There has been proposed a method for displaying patient medical crisis automatically under an electronic data bank for patient data (EPR) and under using an expert system stimulating medical examinations that are doubtful according to various data combinations through proceeded medical examinations or grown crisis of diseases, wherein by each inputting of new data into EPR, these new medical data are simultaneously transferred to the expert system started with all of patient data that is previously stored, the system informs the new data to, for example, an input device, to a patient or to a doctor when changing crisis evaluation (For example, see Patent Reference 3).

However, in Patent Reference 1, the use state (for example, number of times of use per day) of the lavatory and going-out state (for example, whether the managed person is out or not) of the managed person are mainly detected by the action detection sensor, and the health managing apparatus is only an action management system for judging whether the states are different from a usual life rhythm. Although the health managing apparatus is used as a health (living) management system when the managed person is an elderly person, the health managing apparatus is a mere action management system when the managed person is a health person.

In Patent Reference 2, the information capable of being obtained by utilizing the vital sensor is limited to blood pressure, body temperature, cardiac rate and arterial blood oxygen saturation degree or the like which are specified in Patent reference 2, and thereby it is difficult to obtain information regarding ingredients in biologic fluid. Also, the upper limit and lower limit of each measurement item are determined to decide only the normal region by using the temporal data of each measurement item as reference for each managed person (measurer). Furthermore, the determinate measurement item is verified for each measurement item according to the normal region, and the relativeness between the measurement items is not analyzed. Also, the contents of the information (output) part according to the data are not described by the mere judgment of data.

In Patent Reference 3, the consistency with past history data is verified by comprehensively accumulating individual (patient) information due to an electronic chart system with medical site in mind using the expert system. It is difficult to utilize the method as the support system of the health management of the individual every day. Also, the method is a mere data management system, and neither an analyzing method nor an output technique is described in Patent Reference 3.

Although it is necessary to consider the leak of information when accumulating and managing the individual data, particularly bear in mind that the information of the individual is the greatest property belonging to the individual, an individual consent system accompanying individual information disclosure is not considered at all in the conventional systems.

Patent Reference 1

Japanese Unexamined Patent Application Publication No. 2003-271747

Patent Reference 2

Japanese Unexamined Patent Application Publication No. 2002-233509

Patent Reference 3

Japanese Unexamined Patent Application Publication No. 2002-15074

DISCLOSURE OF THE INVENTION

Problems to be Solved by the Invention

The present invention has been accomplished in view of the foregoing and other problems. It is an object of the present invention to provide a method for recognizing/analyzing a plurality of data concerning health management of an individual as his/her individual characteristic pattern data while considering the relationship between the data instead of analyzing each of the data separately; a health support method provided by the method; and a system thereof.

Means for Solving the Problems

In the present invention, so as to solve the problems, a health support method comprises: a support computer for judging a health condition according to received health data of an individual and supporting a health promotion to the individual; and a user terminal connected to the support computer via a communication network, wherein the support computer stores the individual health data acquired in advance in individual data storage means, subjects the individual heath data extracted from the individual data storage means to a multivariate analysis, thereby setting a reference space of the individual, which is stored in reference data storage means, calculates a Mahalanobis' generalized distance from the reference space of the individual read out from the reference data storage means for the individual health data received from the user terminal, and judges the health condition of the individual according to the distance.

Herein, for example, techniques such as a quantification II classification due to a technique of discriminant analysis can be used for the multivariate analysis for setting the individual reference space. After a plurality of variables deriving from each individual are categorized, the profiling of the categorized variables as the individual characteristics is carried out. Also, the Mahalanobis' generalized distance bears a major role for specifying the result of the profiling of a plurality of variables deriving from the individual according to a decided condition (for example, health or the like) as the reference space on a space coordinate axis and objectively comparing the result with a space formed by a plurality of variable groups by comparing and verifying. Thereby, in the present invention, a state where the individual can recognize well according to the characteristics that each individual has is patternized by using a plurality of variables, and thereby the patternized state can be managed as the individual reference space.

Herein, it is preferable that when the health data includes non-digitized data, the support computer digitizes the data on a prejudged scale.

Also, it is preferable that the support computer extracts specific health data regarding the received data of the health data stored in the individual data storage means according to the received individual health data, and sets the reference space of the individual for the extracted specific health data using the multivariate analysis.

More particularly, it is preferable that the support computer sets a prejudged permission range from the set reference space of the individual, stores the permission range in the reference data storage means, compares the calculated Mahalanobis' distance with the permission range for the received individual health data, and judges the health condition of the individual according to the comparison.

Also, it is preferable that a management computer for storing and managing information regarding the commodity or service regarding health is connected to the support computer via a communication network, the support computer transmits information regarding the judged health condition of the individual to the management computer, and the management computer specifies information regarding a commodity or service suitable for the condition according to the information regarding the received health condition of the individual.

Specifically, it is preferable that the support computer or the management computer transmits the information regarding the health condition judged by the support computer or the information regarding the commodity or service specified by the management computer to the accessed user terminal.

Furthermore, it is preferable that a card reader for reading information of an integrated recording card storing individual biometrics information and access information to the support computer or the management computer to the user terminal is connected to a scanner for acquiring the individual biometrics information, the user terminal collates the biometrics information inputted from the card reader with the information inputted from the scanner, and accesses the support computer or the management computer according to the access information similarly inputted from the card reader when the biometrics information corresponds to the information inputted from the scanner.

The present invention provides a health support system comprising: a support computer for judging a health condition according to received health data of an individual and supporting a health promotion to the individual; and a user terminal connected to the support computer via a communication network, the support computer includes: individual data storage means for storing the individual health data acquired in advance; means for subjecting the individual heath data extracted from the individual data storage means to a multivariate analysis, thereby setting a reference space of the individual; reference data storage means for storing the set reference space; means for calculating a Mahalanobis' generalized distance from the reference space of the individual read out from the reference data storage means for the individual health data received from the user terminal; and means for judging the health condition of the individual according to the calculated Mahalanobis' generalized distance.

Herein, it is preferable that an input terminal into which the individual health data is inputted is connected via communication with the user terminal, and the user terminal transmits the health data received from the input terminal to the support computer.

Also, it is preferable that a management computer connected to the support computer via the communication network is provided, and wherein the management computer comprises information storage means for storing and managing information regarding a commodity or service regarding health, and means for receiving information regarding the health condition of the individual judged by the support computer to specify information regarding the commodity or service suitable for the condition from the information storage means.

Also, it is preferable that the information regarding the commodity or service stored and managed in the management computer is regarding at least one commodity or service selected from a health-related commodity, an exercise program, a life consultation, and a medical agency and an alternative medical agency.

Furthermore, it is preferable that a card reader for reading the information of an integrated recording card storing individual biometrics information and access information to the support computer or the management computer to the user terminal is connected to a scanner for acquiring the individual biometrics information, and the user terminal collates the biometrics information inputted from the card reader with the information inputted from the scanner, and accesses the support computer or the management computer according to the access information similarly inputted from the card reader when the biometrics information corresponds to the information inputted from the scanner.

Also, it is preferable that the health data of the individual are a plurality of data selected from saliva analysis data, blood analysis data, weight data, blood pressure data, body temperature data, data regarding the number of times of eating, quality and quantity, data regarding the number of times and frequency of excretion, data regarding sleep, the number of walk (quantity of motion), and data regarding an oral condition and oral hygiene.

Effects of the Invention

According to the health support method and system thereof according to the present invention described above, although the data obtained from the conventional each information (measurement item) is recognized as an original variable, there is no example analyzing as the individual data based on the mutual complicated relationship. On the other hand, since the health reference value and health change value of each individual can be set and utilized as the individual reference space to the individual health by digitizing the plurality of acquired information to carry out profiling as the individual characteristics, not a mere anagnorisis system of an abnormal value in each individual but daily comprehensive self-health management can be attained.

BEST MODE FOR CARRYING OUT THE INVENTION

Figure 1:
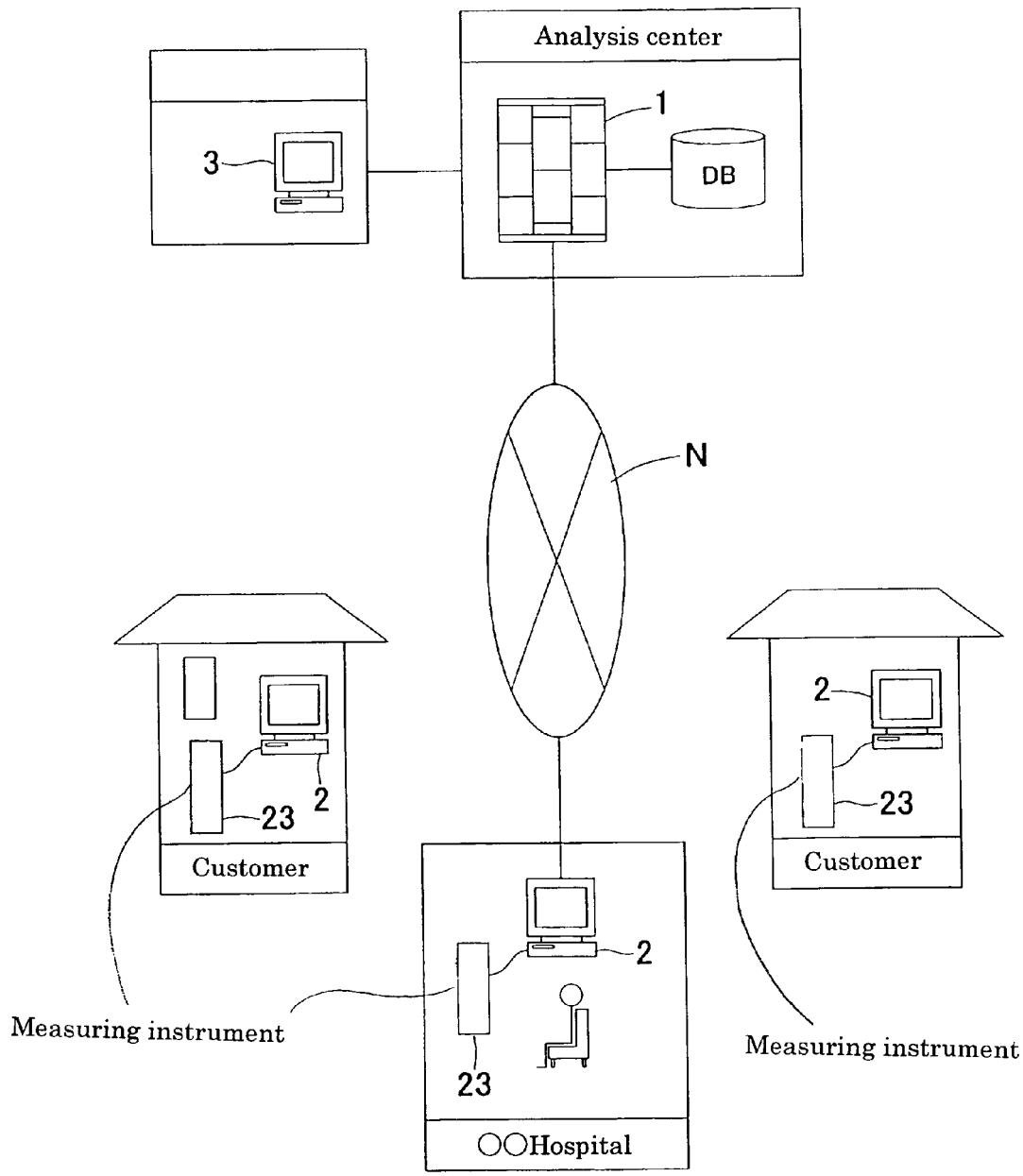
FIG. 1 shows the whole system constitution of a health support system according to a representative embodiment of the present invention.

Next, an embodiment of the present invention will be described in detail according to the accompanying drawings. FIG. 1 shows the whole system constitution of a health support system constitution according to the present invention. FIGS. 1 to 8 show a representative embodiment. In FIG. 1, numerals 1, 2, 3 designate a support computer, a user terminal and a management computer, respectively.

As shown in FIG. 1, in a health support system S according to the present invention, the support computer 1 for judging a health condition according to received health data of an individual and supporting a health promotion to the individual, a single or a plurality of user terminals 2 and the management computer 3 are communicatively connected via a communication network N, thereby constituting a support system of a self-propelling health management. The communication network N can utilize, for example, an information transmission system such as the Internet and a private line.

Figure 2:
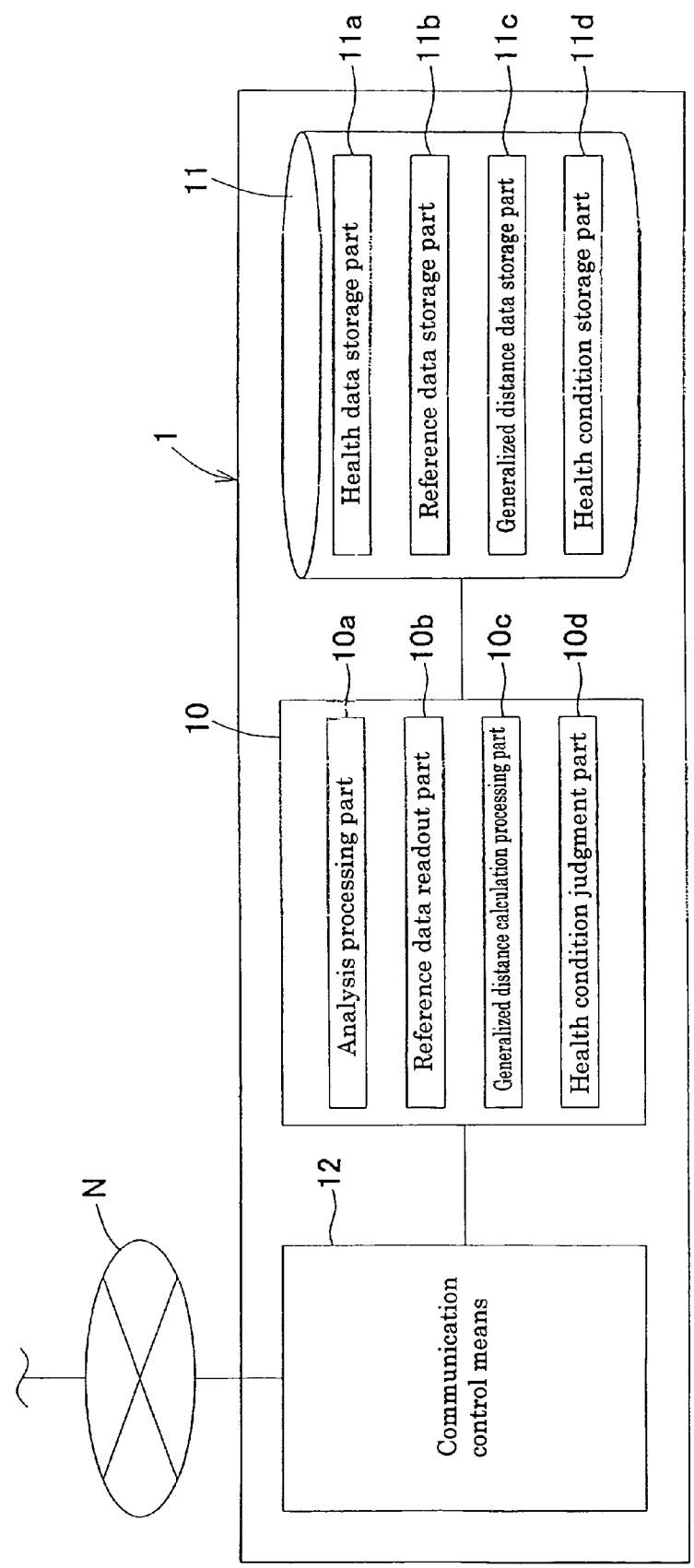
FIG. 2 is a block diagram showing the constitution of a support computer.

As shown in FIG. 2, the support computer 1 is a computer in which a storage means 11 and a communication control means 12 are connected to a processing unit 10. The processing unit 10 mainly comprises a microprocessor, and has a storage part comprising a RAM and a ROM which are not shown and storing programs and processing data for specifying the procedures of various processing operations.

Functionally, the processing unit 10 is provided with an analysis processing part 10a for subjecting individual heath data extracted from a health data storage part 11a to a multivariate analysis, thereby setting a reference space of the individual, a reference data readout part 10b for extracting the reference space regarding the health data of the individual received from the user terminal from a reference data storage part 11b, a generalized distance calculation processing part 10c for calculating a Mahalanobis' generalized distance according to the reference space of the individual read out, and a health condition judgment part 10d for judging the health condition of the individual according to the Mahalanobis' generalized distance taken out from the generalized distance data storage part 11c. These functions are realized by the above program.

The storage means 11 is composed of a health data storage part 11a for storing the health data of the individual acquired in advance, a reference data storage part 11b for storing the reference space set by the analysis processing part 10a, a generalized distance data storage part 11c for storing the Mahalanobis' generalized distance calculated in the generalized distance calculation processing part 10c, and a health condition storage part 11d for storing and managing the data regarding the health condition of the individual judged by the health condition judgment part 10d.

Figure 3:
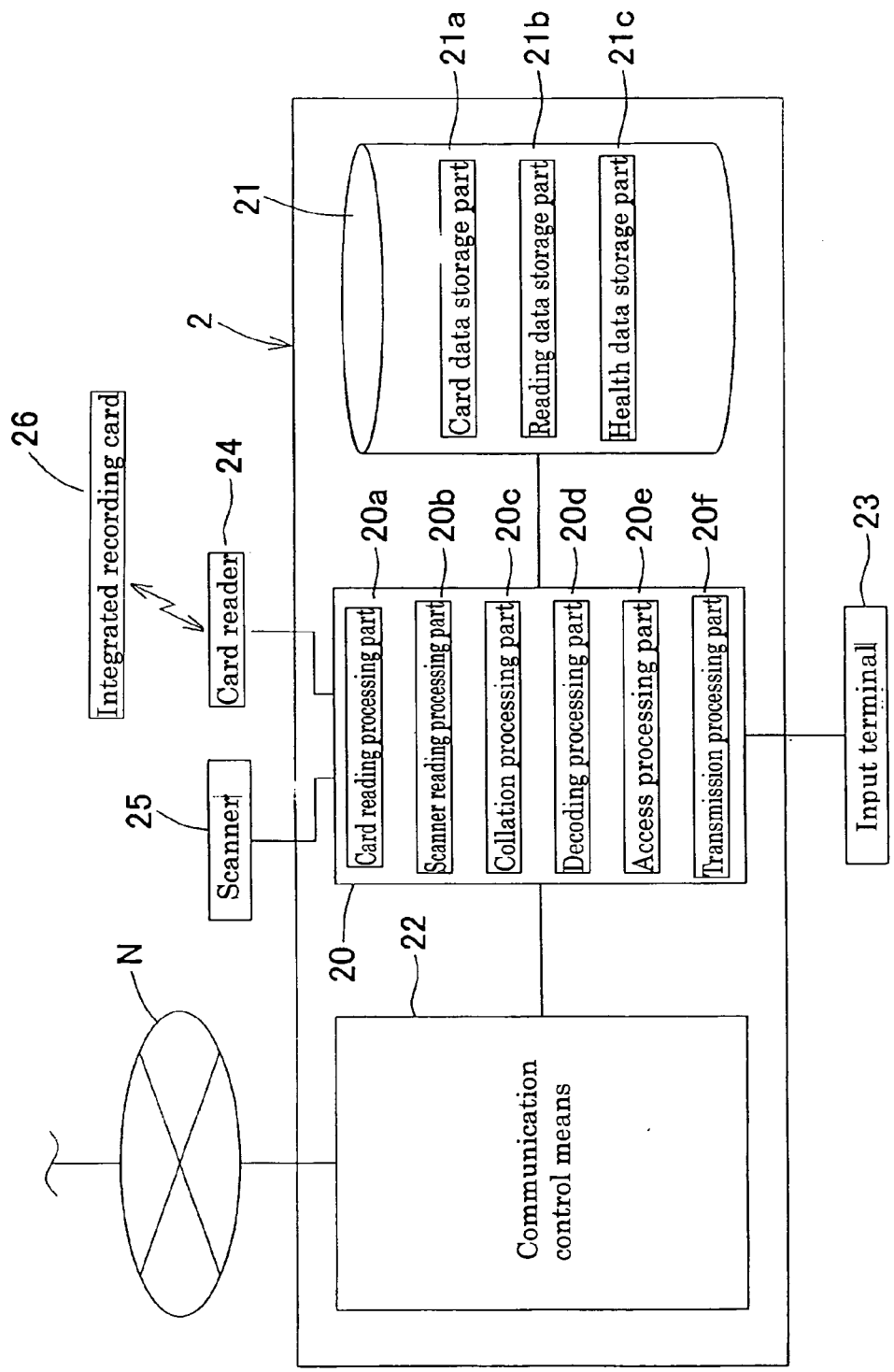
FIG. 3 is a block diagram showing a user terminal and the constitution in the periphery thereof.
Figure 4:
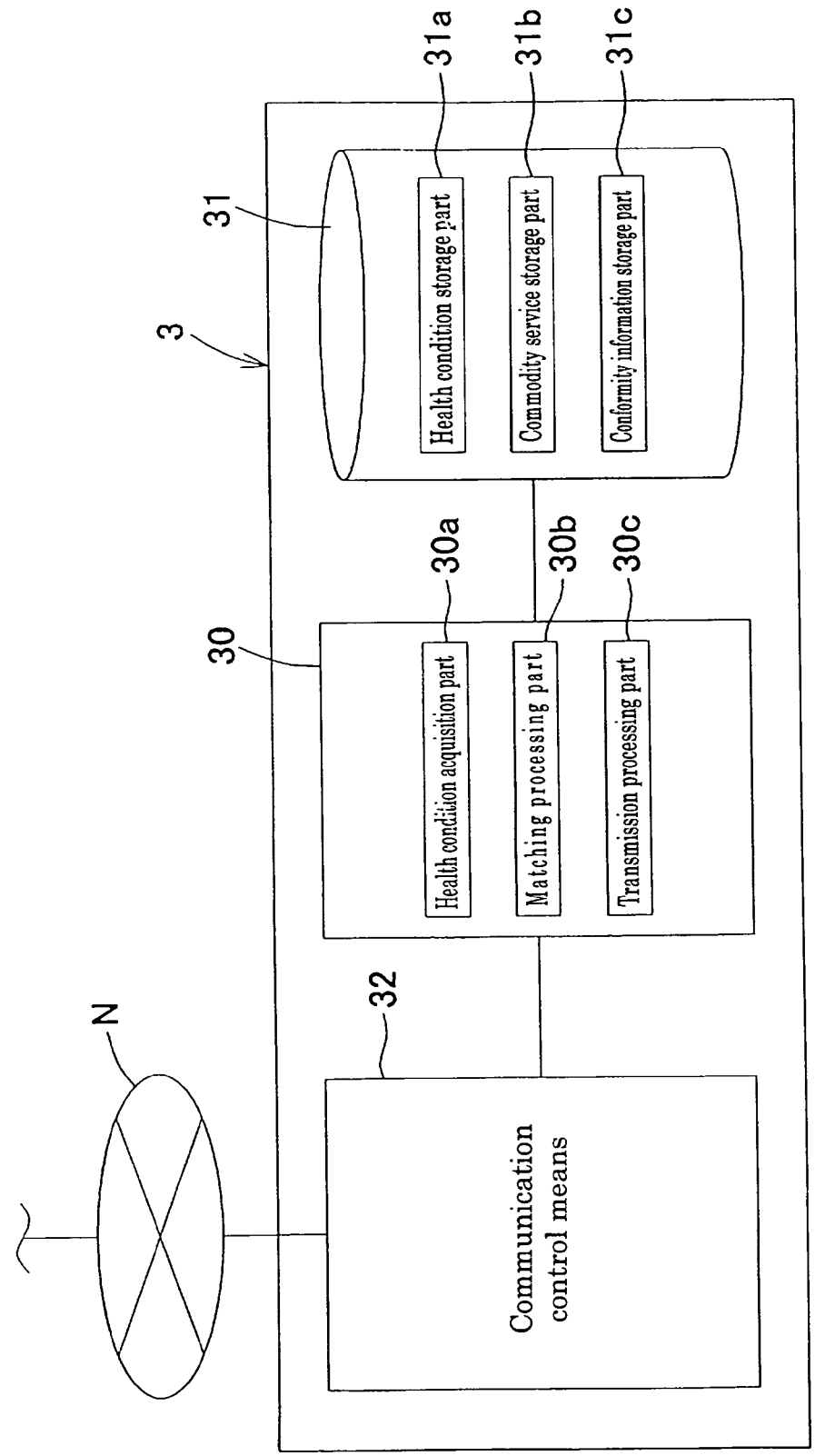
FIG. 4 is a block diagram showing the constitution of a management computer.

Also, as shown in FIGS. 3, 4, the user terminal 2 and the management computer 3 are also respectively a computer in which storage means 21 (31) and communication control means 22 (32) are connected to a processing unit 20 (30) as in the above support computer 1. The processing unit 20 (30) mainly comprises a microprocessor, and has a storage part comprising a RAM and a ROM which are not shown and storing programs and processing data for specifying the procedures of various processing operations.

An input terminal 23 into which the individual health data is inputted, a card reader 24 for reading the information of an integrated recording card 26 and a scanner 25 for acquiring individual biometrics information are connected to the user terminal 2.

For example, conventional various terminal units which can carry out examinations such as asputum examination, a saliva examination, a urine examination, a blood examination, a fecal examination, a plaque examination, a mucosal cell examination, and gene examination can be used for the input terminal 23. An IC card and an optical card or the like can be specifically used for the integrated recording card 26, and the biometrics information respectively enciphered and the access information to the support computer or the management computer are stored in the storage means in the card.

The processing unit 20 of the user terminal 2 is provided with a card reading processing part 20a for making the card data storage part 21a store the enciphered biometrics information and access information inputted from the card reader, a scanner reading processing part 20b for enciphering the biometrics information inputted from the scanner and making the card data storage part 21a store the biometrics information, a collation processing part 20c for comparing and collating the coding information of the biometrics data taken out from the card data storage part 21a and the reading data storage part 21b, a decoding processing part 20d for taking out and decrypting the access information of the card data storage part 21a when the biometrics information from the card data storage part 21a corresponds to the biometrics information from the card data storage part 21a, an access processing part 20e for accessing the support computer or the management computer according to the decrypted access information, a transmission processing part 20f for taking out data in the health data storage part 21c and transmitting the data to the accessed support computer 1 or management computer 3. These functions are realized by the above program.

The storage means 21 of the user terminal 2 comprises a card data storage part 21a for storing the coding information of the biometrics information and access information inputted from the card reader, a reading data storage part 21b for storing and managing the biometrics information enciphered by the scanner reading processing part 20b, and a health data storage part 21c for storing and managing the individual health data inputted from the input terminal 23.

As the health data of the individual inputted from the input terminal 23, there can be used various data such as saliva analysis data, blood analysis data, weight data, blood pressure data, body temperature data, data regarding the number of times of eating, quality and quantity, data regarding the number of times and frequency of excretion, data regarding sleep, the number of walk (quantity of motion), and data regarding oral condition and oral hygiene.

The health data may be obtained by using an exclusive biomechanical material collecting container capable of collecting and storing, collecting the individual biomechanical material, utilizing mails and parcel delivery services or the like to convey the biomechanical material to an analysis center, and directly inputting the data of the inspected result into the support computer 1 from a keyboard or the like except a method for transmitting the health data from the user terminal 2. Thus, the input terminal 23 constitutes an exclusive self-diagnosis inquiry system for everyday life information collection, and transmits each individual report living information to the analysis center. Also, the input terminal 23 utilizes various sensors such as a biosensor as the input terminal 23 to collect the individual everyday life information, and transmits the individual everyday life information to the analysis center. The user terminal 2 may be integrally constituted with the input terminal 23.

The processing unit 30 of the management computer 3 is provided with a health condition acquisition part 30a for receiving the information regarding the individual health condition judged by the support computer 1, a matching processing part 30b for extracting information (matching information) regarding a commodity or service suitable for the received health condition from a commodity service storage part 31b and storing the information, and a transmission processing part 30c for suitably transmitting the matching information of the conformity information storage part 31c to the user terminal 2. These functions are realized by the above program.

The storage means 31 of the management computer 3 is composed of a health condition storage part 31a for storing and managing the information regarding the health condition of the individual received from the support computer, a commodity service storage part 31b for storing and managing the information regarding the commodity or service regarding the health, and a conformity information storage part 31c for storing the matching information extracted by the matching processing part 30b.

The information stored and managed in the commodity service storage part 31b is related to one or two or more commodities or services selected from a health-related commodity, an exercise program, a life consultation and a medical agency and an alternative medical agency.

Hereinafter, the present invention will be described according to the embodiment of the processing procedure in the health support system S.

Figure 5:
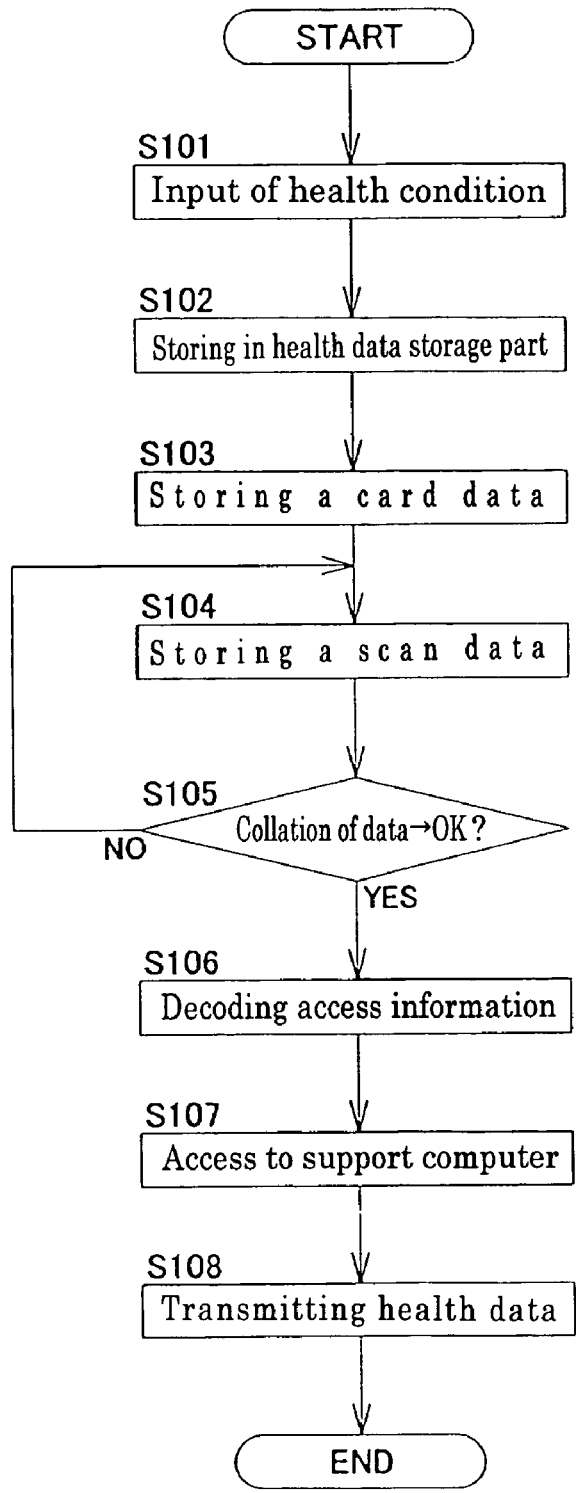
FIG. 5 is a schematic flow diagram showing processing procedures until health data inputted into the user terminal is transmitted to the support computer.

FIG. 5 is a schematic flow diagram showing processing procedures until individual health data inputted into the user terminal 2 is transmitted to the support computer 1.

When the individual health data is inputted from the input terminal 23 (Step 101), the user terminal 2 make the health data storage part 21c store the individual health data (Step 102). In the example, there are used examples of a plurality of data groups in which saliva examination data (for example, CORTISOL and Glycated albumin or the like under sleep), vital data (for example, blood pressure data and body temperature or the like at the time of rising), and living environment data (for example, the number of times of excretion, the number of times and quantity or the like of eating or the like) are inputted a plurality of times (12 to 24 points for six months) of the health data.

In order to transmit the inputted health data to the support computer 1, first, the card reading processing part 20a makes the card data storage part 21a store the enciphered biometrics information and access information inputted from the card reader 24 (Step 103), and the scanner reading processing part 20 enciphers and stores the biometrics information inputted from the scanner 25 (Step 104). Then, the collation processing part 20c compares and collates the coding information of the biometrics data taken out from the card data storage part 21a and the reading data storage part 21b (Step 105). For example, individual identification data such as fingerprint and iris can be used as the biometrics data, and the use of individual character information except the biometrics data is also a desirable embodiment.

When both the coding informations correspond in the comparison and collation of Step 105, the decoding processing part 20d takes out and decrypts the access information of the card data storage part 21a (Step 106). The decoding processing part 20d accesses the support computer 1 using the access information decoded by the access processing part 20e (Step 107), and the transmission processing part 20f takes out the above health data in the health data storage part 21c, and transmits the health data (Step 108). Thus, the individual intention is respected and the mistake is prevented before happens by adopting the structure capable of accessing the support computer 1 after performing an individual consent attestation. It is not necessary to decode to collate and to be enciphered.

Figure 6:
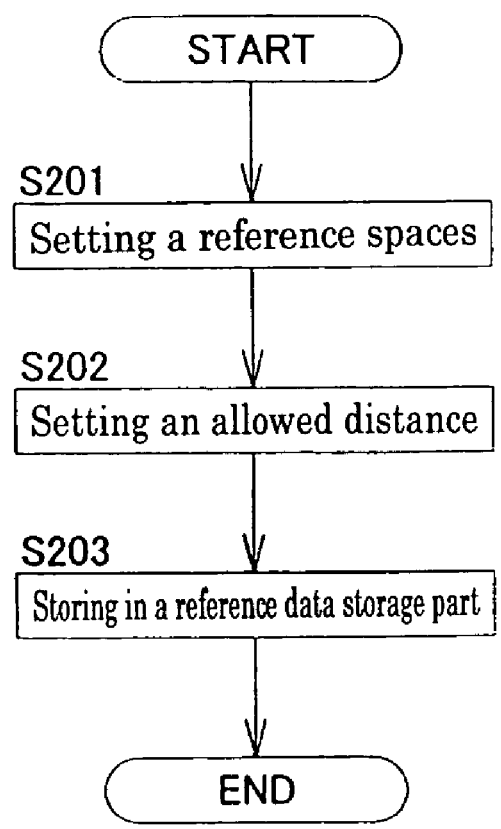
FIG. 6 is a schematic flow diagram showing procedures until a reference space and a permission range are set to individual health data.

Next, FIG. 6 is a schematic flow diagram showing procedures until a reference space and permission range of the individual are set to health data of an individual in the support computer 1.

The analysis processing part 10a subjects the health data of the individual extracted from the health data storage part 11a for storing the individual health data acquired in advance to a multivariate analysis, and sets the reference space of the individual (Step 201). Specifically, in order to produce the reference space of the individual, when the number of the information group (a plurality of individual data selected as a parameter by the original judgement criterion such as the accuracy and characteristics of data) of the individual in the phenomenon recognized to be health is set to n, the average value of each individual data, the standard deviation for each data, and the inverse matrix of a correlation matrix are produced. When the number of data is set to k, and the vector of the average value is represented by $m_1, m_2, \ldots, m_k$, the vector becomes a zero point. When the vector of the standard deviation for each data, the inverse matrix of the correlation matrix and the square of the Mahalanobis's distance are respectively represented as $\sigma_1, \sigma_2, \ldots \sigma_k$, $(\alpha_{ij})$ and $D^2$, $D^2$ can be repre sented by the following formula using data of k item as $x_1, x_2, \ldots, x_k$.

$$D^2 = \frac{1}{k}\sum_{ij} \alpha_{ij}\left(\frac{x_i - m_i}{\sigma_i}\right)\left(\frac{x_j - m_j}{\sigma_j}\right) \quad \text{[Formula 1]}$$

When the information group of the individual as the object of the reference space of the individual is averaged by calculating D2 to number n piece, the average value becomes 1.

$$D_0^2 = \frac{1}{n}(D_1^2 + D_2^2 + \cdots + D_n^2) \quad \text{[Formula 2]}$$

The measure set of the synthetic measurement to the zero point is enabled by using the square root as the distance of a unit.

$$D^2 = \frac{1}{D_0^2} \times \frac{1}{k}\sum_{ij} \alpha_{ij}\left(\frac{x_i - m_i}{\sigma_i}\right)\left(\frac{x_j - m_j}{\sigma_j}\right) \quad \text{[Formula 3]}$$

Herein, when the health data includes the non-digitized data, the above multivariate analysis is carried out after digitizing the data on a prejudged scale.

Also, simultaneously, the analysis processing part 10a sets a prejudged permission range from the set reference space of the individual (Step 202), and makes the reference data storage part 11b store the reference space and the permission range (Step 203). Specifically, if the selection criterion of the set object number (n) is exact while the measurement accuracy and stability of each individual data are maintained, the average of D2 obtained by the above analysis technique is infinitely converged on a zero point, and is set as the individual reference space. Also, the region of the dispersion vector from the zero point can be recognized as the permission range. Instead of setting the reference space in advance, the specific health data concerning the received data may be extracted, and the reference space of the individual may be set by subjecting the extracted specific health data to the multivariate analysis.

Figure 7:
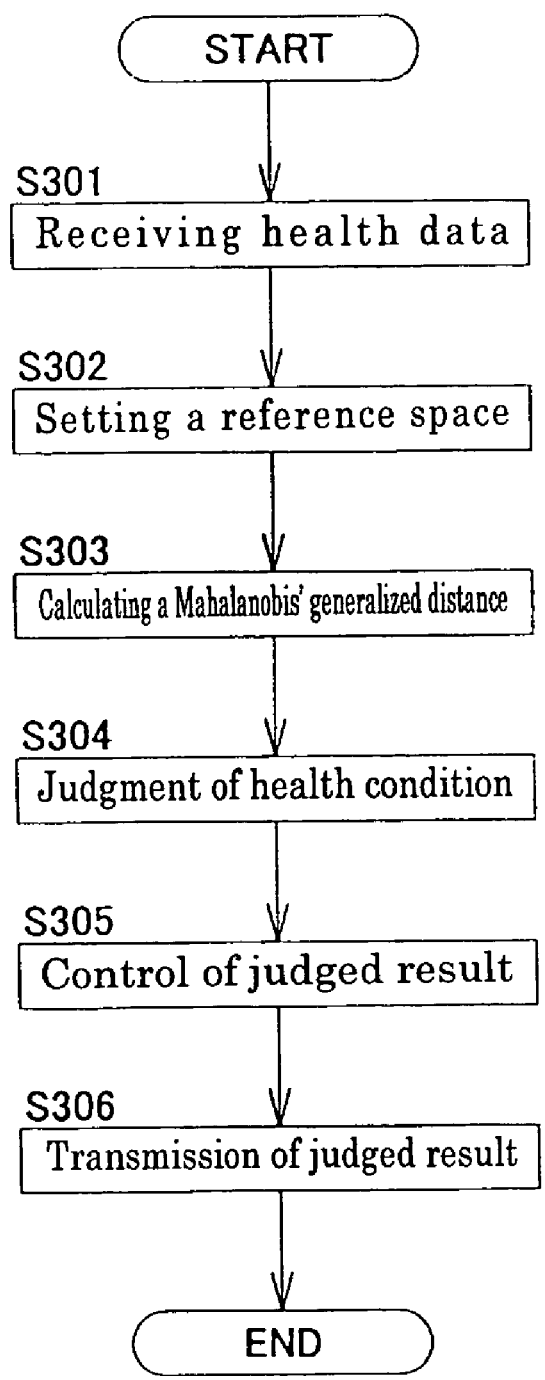
FIG. 7 is a schematic flow diagram showing a procedure until a Mahalanobis' generalized distance is calculated and an individual health condition is judged.

Next, FIG. 7 is a schematic flow diagram showing procedures until the Mahalanobis' generalized distance is calculated using the individual reference space and the health condition of the individual is judged according to the distance.

Figure 8:
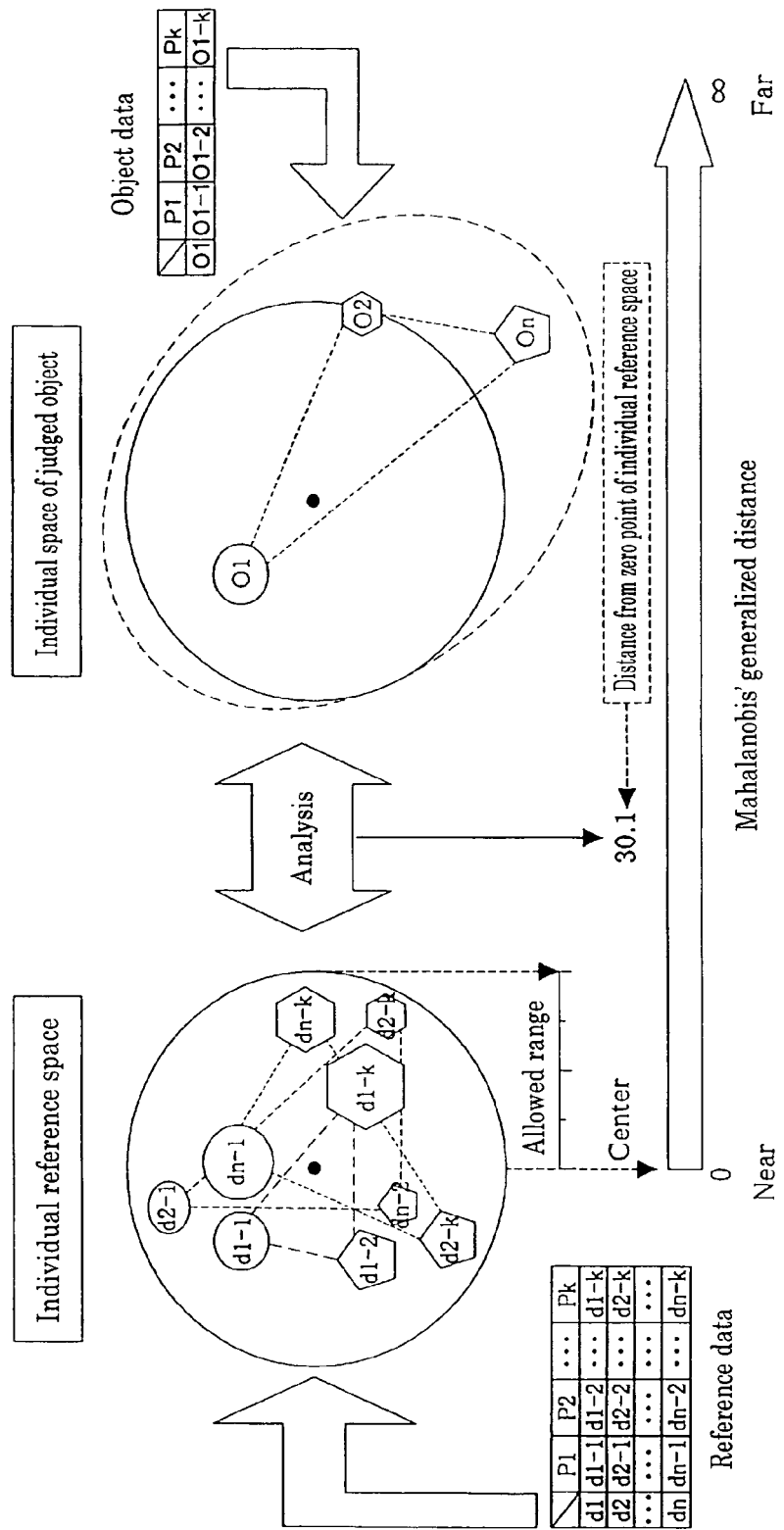
FIG. 8 is a schematic flow diagram showing processing procedures when an individual reference space and an individual space to be judged carrying out a (health) judgment are evaluated by using the Mahalanobis's generalized distance.

When the support computer 1 receives the health data from the user terminal 2 (Step 301), the reference data readout part 10b extracts the reference space regarding the health data of the individual received from the user terminal from the reference data storage part 11b (Step 302), and the generalized distance calculation processing part 10c calculates the Mahalanobis' generalized distance according to the reference space of the individual read (Step 303). Specifically, the Mahalanobis' generalized distance from the zero point of the individual reference space (D2) obtained by the above analysis technique to the zero point of the object space produced by the object data of the individual measured in an optional phenomena is calculated (FIG. 8).

The health condition judgment part 10d judges the health condition of the individual according to the Mahalanobis' generalized distance (Step 304). Specifically, it can be judged that when the Mahalanobis' generalized distance is smaller, the phenomenon as the object of the individual is health and when the Mahalanobis' generalized distance exceeds the permission range and is larger, the phenomenon as the object of the individual is not health.

The judged health condition is stored and managed in the health condition storage part 11d (Step 305), and is suitably transmitted to the management computer (Step 306).

Figure 9:
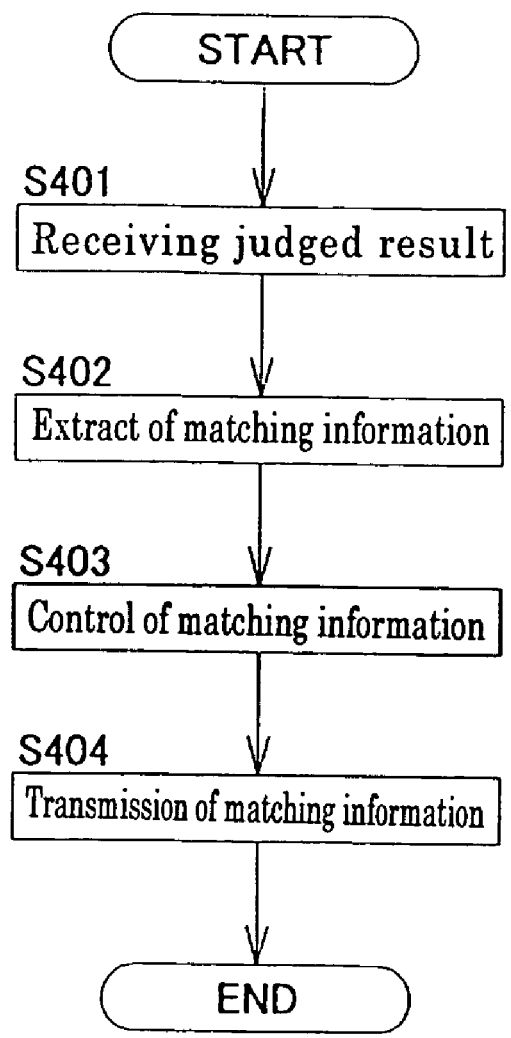
FIG. 9 is a schematic flow diagram showing processing procedures until information regarding a commodity or service suitable for a health condition is provided.

Next, FIG. 9 is a schematic flow diagram showing processing procedurea until the information regarding the commodity or service suitable for the judged health condition is provided to the user terminal 2 from the management computer 3.

When the health condition acquisition part 30a receives the information (the information or the like not being health for the individual) regarding the individual health condition judged by the support computer 1 (Step 401), the matching processing part 30b extracts the information (matching information) regarding the commodity or service suitable for the received health condition from the commodity service storage part 31b (Step 402), and makes the information the conformity information storage part 31c store the information (Step 403).

Examples of the commodities or services include health foods, health commodities such as teeth brushing, tooth brushes, medicinal products and supplements; information regarding exercise programs, life consultations, health of mouth cavity and whole body and disease risk, and the provide of information regarding the risk reduction methods; the introduction of doctors, dentists, medical agencies and alternative medical agencies or the like; the introduction of life sickness insurances for health management and support; and health management support services linked to the life sickness insurances.

In the example, in the case of the individual having type II diabetes as a previous disease, the fault of diabetes control can be indicated by providing information that the health condition is impaired. For example, when the Mahalanobis' generalized distance to the individual space to be judged in an optional phenomena is maximized from the reference space which is the health of the individual, it can be predicted that the state is clearly being deviated from the health state, and the necessity for a close examination can be informed. When the Mahalanobis' generalized distance tends to be extended, the health food and health commodity for diabetes can be also recommended.

The transmission processing part 30c suitably transmits the matching information of the conformity information storage part 31c to the accessing user terminal 2 (Step 404).

The present invention may provide the same function as the above management computer 3 in the support computer 1, and may provide above matching information to the user terminal 2 from the support computer 1 directly.

What is claimed is:

1. A health support method for an individual person, using multi-variate analysis and comprising:
providing a support computer to judge a health condition of the individual person according to received health data of the individual person;
providing a user terminal connected to the support computer via a communication network;
acquiring, in advance, individual healthy reference data of the individual person while in a healthy state, the reference data comprising a plurality of variables, the variables being related to more than one organ of the body and/or more than one type of measurement;
determining a single reference space zero point of the individual person from the healthy reference data by running a program embedded in the support computer that subjects the reference data extracted from an individual data storage means to a multivariate analysis, thereby setting the reference space zero point of the individual person;

storing the reference space zero point in a reference data storage means;

inputting object data of the individual person while in an unknown state of health, the object data comprising the plurality of variables;

calculating, as a single number, a multivariate Mahalanobis generalized distance of the object data of the individual person from the reference space zero point of the individual person, forming a judgment about the health condition of the individual person as a function of a magnitude of the Mahalanobis generalized distance between the object data and the reference space zero point, wherein a lesser magnitude of the single number is associated more with a healthy state and a greater magnitude of the single number is associated more with an unhealthy state; and outputting the judgment, thereby supporting a health promotion to the individual person.

2. The health support method according to claim 1, wherein when the health data includes non-digitized data, the support computer digitizes the data on a prejudged scale.

3. The health support method according to claim 2, wherein the support computer extracts specific health data regarding the received data of the health data stored in the individual data storage means according to the received individual health data, and sets the reference space zero point of the individual for the extracted specific health data using the multivariate analysis.

4. The health support method according to claim 2, wherein the support computer sets a prejudged permission range from the set reference space zero point of the individual, stores the permission range in the reference data storage means, compares the calculated distance with the permission range for the received individual health data, and judges the health condition of the individual according to the comparison.

5. The health support method according to claim 2, comprising a management computer for storing and managing information regarding a commodity or service regarding health that is connected to the support computer via a communication network, wherein the support computer transmits information regarding the judged health condition of the individual to the management computer, and wherein the management computer specifies information regarding a commodity or service suitable for the condition according to the information regarding the received health condition of the individual.

6. The health support method according to claim 5, wherein the support computer or the management computer transmits the information regarding the health condition judged by the support computer or the information regarding the commodity or service specified by the management computer to the accessed user terminal.

7. The health support method according to claim 1, wherein the support computer extracts specific health data regarding the received data of the health data stored in the individual data storage means according to the received individual health data, and sets the reference space zero point of the individual for the extracted specific health data using the multivariate analysis.

8. The health support method according to claim 1, wherein the support computer sets a prejudged permission range from the set reference space zero point of the individual, stores the permission range in the reference data storage means, compares the calculated distance with the permission range for the received individual health data, and judges the health condition of the individual according to the comparison.

9. The health support method according to claim 1, comprising a management computer for storing and managing information regarding a commodity or service regarding health that is connected to the support computer via a communication network, wherein the support computer transmits information regarding the judged health condition of the individual to the management computer, and wherein the management computer specifies information regarding a commodity or service suitable for the condition according to the information regarding the received health condition of the individual.

10. The health support method according to claim 9, wherein the support computer or the management computer transmits the information regarding the health condition judged by the support computer or the information regarding the commodity or service specified by the management computer to the accessed user terminal.

11. The health support method according to claim 10, wherein a card reader for reading information of an integrated recording card storing individual biometrics information and access information to the support computer or the management computer to the user terminal are connected to a scanner for acquiring the individual biometrics information, the user terminal collates the biometrics information inputted from the card reader with the information inputted from the scanner, and accesses the support computer or the management computer according to the access information similarly inputted from the card reader when the biometrics information corresponds to the information inputted from the scanner.

12. The health support method according to claim 1, wherein the Mahalanobis' generalized distance is used for specifying the result of the profiling of a plurality of variables deriving from the individual according to a condition of health.

13. A health support system for an individual person, using multi-variate analysis and comprising:

a support computer to judge a health condition of the individual person according to received health data of the individual person;

a user terminal connected to the support computer via a communication network, whereby the system acquires, in advance, individual healthy reference data of the individual person while in a healthy state, the reference data comprising a plurality of variables, the variables being related to more than one organ of the body and/or more than one type of measurement;

wherein the support computer includes:

individual data storage means for storing the reference data acquired in advance;

a program to determine a single reference space zero point of the individual person from the healthy reference data by subjecting the reference data extracted from the individual data storage means to a multivariate analysis, thereby setting the reference space zero point of the individual person;

reference data storage means for storing the set reference space zero point;

the program also calculating, as a single number, a multivariate Mahalanobis generalized distance from the reference space zero point of the individual person, and;

the program also judging the health condition of the individual as a function of a magnitude of the calculated Mahalanobis generalized distance between object data of the individual person while in an unknown state of health, the object data comprising the plurality of variables, and the reference space zero point, thereby supporting a health promotion to the individual person, wherein a lesser magnitude of the single number is associated more with a healthy state and a greater magnitude of the single number is associated more with an unhealthy state.

14. The health support system according to claim 13, comprising an input terminal into which the individual health data is inputted that is connected via communication with the user terminal, whereby the user terminal transmits the health data received from the input terminal to the support computer.

15. The health support system according to claim 14, comprising a management computer connected to the support computer via the communication network, wherein the management computer comprises information storage means for storing and managing information regarding a commodity or service regarding health, and means for receiving information regarding the health condition of the individual judged by the support computer to specify information regarding the commodity or service suitable for the condition from the information storage means.

16. The health support system according to claim 14, wherein a card reader for reading the information of an integrated recording card storing individual biometrics information and access information to the support computer or the management computer to the user terminal are connected to a scanner for acquiring the individual biometrics information, and wherein the user terminal collates the biometrics information inputted from the card reader with the information inputted from the scanner, and accesses the support computer or the management computer according to the access information similarly inputted from the card reader when the biometrics information corresponds to the information inputted from the scanner.

17. The health support system according to claim 14, wherein the health reference data of the individual person consist of a plurality of data selected the group consisting of from saliva analysis data, blood analysis data, weight data, blood pressure data, body temperature data, data regarding the number of times, quality, and quantity of eating, data regarding the number of times and frequency of excretion, data regarding sleep, the number of walk (quantity of motion), and data regarding an oral condition and oral hygiene.

18. The health support system according to claim 13, comprising a management computer connected to the support computer via the communication network, wherein the management computer comprises information storage means for storing and managing information regarding a commodity or service regarding health, and means for receiving information regarding the health condition of the individual judged by the support computer to specify information regarding the commodity or service suitable for the condition from the information storage means.

19. The health support system according to claim 18, wherein the information regarding the commodity or service stored and managed in the management computer is regarding at least one commodity or service selected from a health-related commodity, an exercise program, a life consultation, and a medical agency and an alternative medical agency.

20. The health support system according to claim 13, wherein a card reader for reading the information of an integrated recording card storing individual biometrics information and access information to the support computer or the management computer to the user terminal are connected to a scanner for acquiring the individual biometrics information, and wherein the user terminal collates the biometrics information inputted from the card reader with the information inputted from the scanner, and accesses the support computer or the management computer according to the access information similarly inputted from the card reader when the biometrics information corresponds to the information inputted from the scanner.

21. The health support system according to claim 13, wherein the health reference data of the individual person consist of a plurality of data selected the group consisting of from saliva analysis data, blood analysis data, weight data, blood pressure data, body temperature data, data regarding the number of times, quality, and quantity of eating, data regarding the number of times and frequency of excretion, data regarding sleep, the number of walk (quantity of motion), and data regarding an oral condition and oral hygiene.

22. The health support system according to claim 13, wherein the Mahalanobis' generalized distance is used for specifying the result of the profiling of a plurality of variables deriving from the individual according to a condition of health.

* * * * *